United States Patent [19]

Schiller

[11] Patent Number: 4,772,277
[45] Date of Patent: Sep. 20, 1988

[54] CHEST CAVITY EVACUATION APPARATUS WITH RESETTABLE AIR VOLUME METER

[75] Inventor: Thomas M. Schiller, Fort Myers, Fla.

[73] Assignee: Vanderbilt University, Nashville, Tenn.

[21] Appl. No.: 87,608

[22] Filed: Aug. 20, 1987

[51] Int. Cl.$^4$ .............................................. A61M 1/00
[52] U.S. Cl. ..................................... 604/321; 604/319; 116/276; 73/323; 73/334
[58] Field of Search ................ 604/321, 319, 320; 116/276; 73/323, 334

[56] References Cited

U.S. PATENT DOCUMENTS

| | | | |
|---|---|---|---|
| 3,683,913 | 8/1972 | Kurtz et al. | 604/321 |
| 3,783,870 | 1/1974 | Schachet | 604/321 |
| 4,455,141 | 6/1984 | Todd | 604/319 |

Primary Examiner—Albert W. Davis, Jr.
Attorney, Agent, or Firm—Tilton, Fallon, Lungmus & Chestnut

[57] ABSTRACT

A chest cavity evacuation apparatus is provided with an air meter which is capable of directly measuring the volume of removed air. Small volumes of evacuated air are collected and measured, and the volume meter is resettable by tilting of the apparatus.

8 Claims, 2 Drawing Sheets

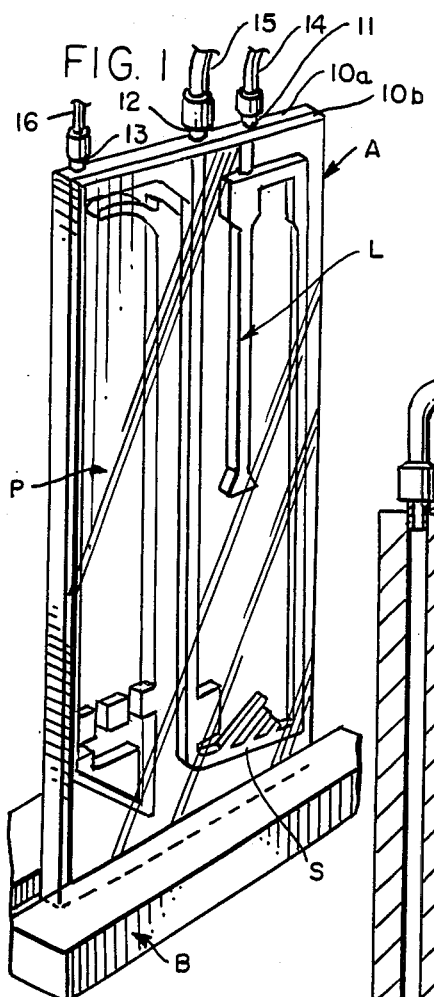
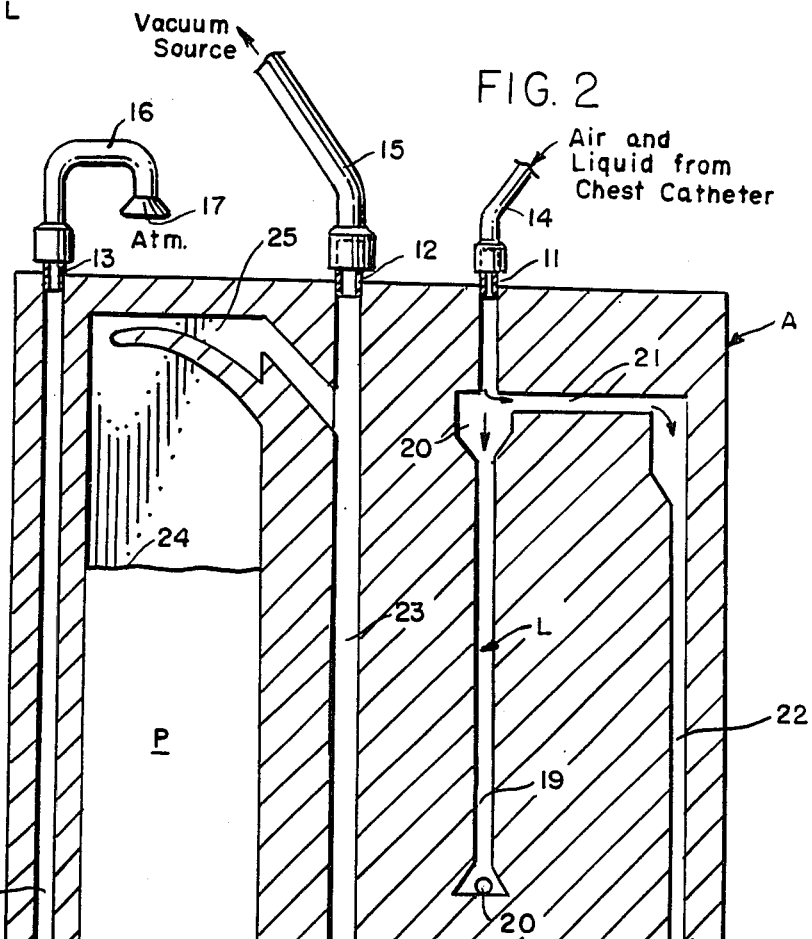
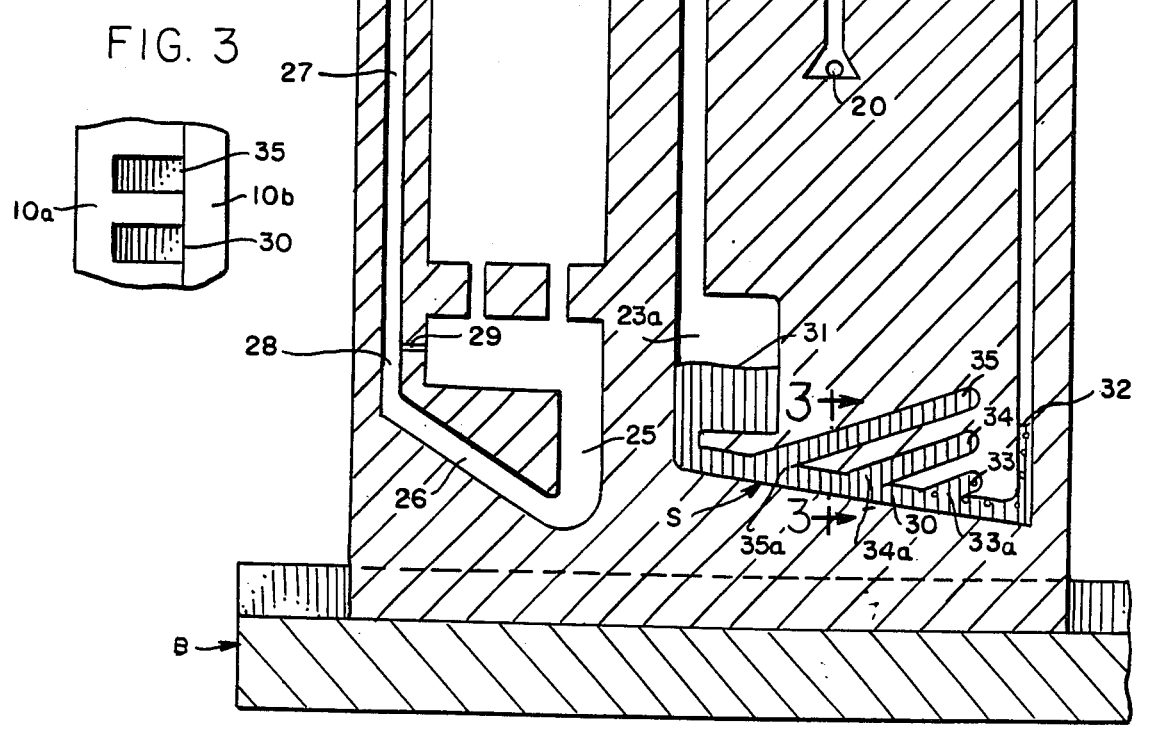

CHEST CAVITY EVACUATION APPARATUS WITH RESETTABLE AIR VOLUME METER

FIELD OF INVENTION

The field of this invention is chest or pleural cavity evacuation apparatus for removing air and liquid. The invention is particularly concerned with the metering of the amount of air removed from the chest cavity.

BACKGROUND OF INVENTION

Chest drainage systems are in widespread use, and are available commercially from a number of manufacturers in the United States and other countries. Such systems include a thoracic catheter which is implanted in the chest cavity, and a water-sealed evacuation apparatus for removing air and liquid. The water-seal chamber communicates on one side with the catheter and on the other side with a source of controlled vacuum. In addition to the water-seal chamber, there may be provided a fluid collection chamber and a vacuum regulator chamber. If the vacuum is supplied through a pressure-regulator valve, the manometer chamber may be eliminated. Most commercial apparatus are at least "two bottle" systems, including a fluid collection chamber and a water-seal chamber. If they also include a pressure regulator chamber, they are commonly referred to as a "three-bottle system".

Application of a chest cavity evacuation system is required following: (1) surgical or traumatic opening of the thoracic cavity; or (2) life-threatening internal rupture of the lung tissue (pneumothorax) which may be spontaneous, or secondary to ventilator barotrauma (very common in premature infants), emphysema or infection. (Hydrothorax, chylothorax, and hemothorax are also indications for chest tube therapy.) Air and/or fluid in the pleural space is life-threatening and requires immediate placement of a pleural catheter with evacuation apparatus for the duration of the underlying problem.

In all of the foregoing applications, it is important to monitor the amount of air and/or fluid being removed from the chest cavity as an indicator of the course of the underlying process and need of continued therapy. When a fluid collection chamber is provided, it can be calibrated so that the amount of removed fluid can be visually determined. Accurate metering of the removed air, however, presents a more difficult problem. The air evacuated bubbles through the water-seal, and therefore a qualitative observation that air is being removed can be visually confirmed. But heretofore there has been no satisfactory metering device for quantitatively measuring the volume of removed air.

U.S. Pat. No. 3,683,913 discloses a chest evacuator having an air-flow meter associated with a water-seal chamber. By utilizing a series of air-flow passages progressively increasing in diameter away from the position of air entry into the water-seal, observation of the number of chambers in which the air is passing out of the water-seal can be used to give a rough estimate of the air flow rate. Chest drainage apparatus incorporating this kind of flow-rate meter has been marketed commercially in the United States. At high air flow rates, by determining and recording the estimated flow rates at the start and end of an observation period, the approximate total volume of evacuated air can be calculated. This kind of flow rate metering, however, is not defined at low flow rates, such as are encountered near the critical time for removal of the chest drainage unit, or during most of the time of use of a pediatric/neonatal drainage unit.

What has been needed is a convenient low volume meter which can be used to accurately determine low volume flows. As the volume of removed air decreases and approaches zero, it is difficult to observe even the small amount of bubbling through the water-seal, or to estimate the rate of flow by a metering device like the one described in U.S. Pat. No. 3,683,913.

It is important to determine the end point of use of the chest evacuation apparatus. When no more air is being removed from the chest cavity, this indicates that the desired negative pressure condition has been restored in the chest cavity. At flow rates of a few milliliters per hour, bubbling in the water-seal is infrequent (e.g., one bubble every few minutes). The attending nurse may need to spend an undue amount of time trying to observe the operation of the drainage unit and frequently records inaccurate observations. However, heretofore no metering device has been provided which permits the nurse to make inspections at intervals of several hours even though the conclusion of the air removal is approximate.

If it is erroneously concluded that no more air is being removed, whereas a small volume flow is actually occurring, this can lead to premature discontinuance of the use of the chest cavity evacuation apparatus with removal of the catheter. Such premature removal, when later discovered, can result in an acute emergency (tension pneumothorax), and will require reinsertion of the catheter and re-establishment of the chest cavity drainage. This is a costly and potentially fatal hospital situation which is very desirable to avoid.

Further, once the fact has been confirmed that no air is being removed from the chest cavity, it is imperative to remove the catheter and discontinue use of the chest evacuation apparatus in a short time, usually within 12 to 24 hours. The risk of chest catheter infection increases with duration of placement, necessitating prompt removal of the catheter upon resolution of the underlying problem. Heretofore, however, the available chest drainage units have sometimes been left connected for longer times than required in order to ascertain that air removal had concluded, thus placing the patient at higher risk of morbidity and mortality from chest catheter complications.

SUMMARY OF INVENTION

This invention provides a chest cavity evacuation apparatus with an air meter which is capable of directly measuring the volume of removed air. This kind of air volume measurement is believed to be a new concept in the clinical management of pleural air leaks. The air volume meter of the invention is adapted for collection and quantitation of extremely small volumes of evacuated air, viz. as little as 1 to 12 milliliters.

An important feature of the volume meter of the present invention is that it is easily resettable. The amount of air removed can be visually observed and recorded, and the meter reset for the next collection period. Thereby, the trend of air removal can be accurately observed, thus giving the clinician a new tool to follow the unpredictable course of a pneumothorax and greater accuracy in the appropriate removal of the catheter. Premature removal of the apparatus can be avoided, while at the same time the apparatus does not remain in use for longer than necessary. When the collected volume of air becomes insignificant over a representative period of time, such as 4 to 6 hours, the use of the apparatus can be continued for a few more hours, and then removed. This represents a considerable improvement in hospital practice.

THE DRAWINGS

A preferred embodiment of the improved chest evacuation apparatus of this invention is shown in the accompanying drawings, in which FIG. 1 is a perspective view of a 3-bottle type evacuation apparatus, which includes a water-seal chamber that has been modified to provide the novel air volume meter of this invention;

FIG. 2 is the enlarged vertical sectional view of the apparatus of FIG. 1, illustrating the internal passage construction, and particularly the water-seal chamber and associated air volume meter;

FIG. 3 is a detailed sectional view taken on line 3—3 of FIG. 2 showing the air-flow passage and one of the air traps;

DETAILED DESCRIPTION

Figure 4:
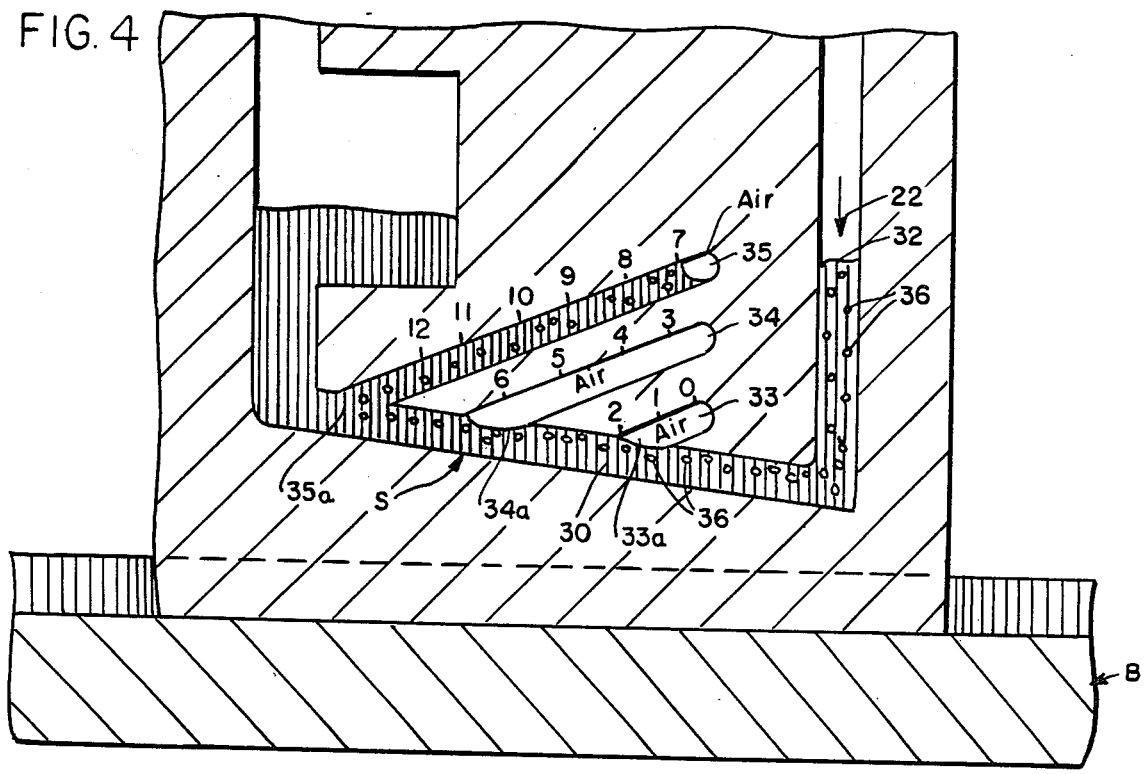
FIG. 4 is an enlarged sectional view of the water-seal and air volume meter, the apparatus being shown in its normal operating position.

The chest cavity evacuation apparatus of this invention includes a water-seal chamber equipped with an air volume meter. This combination is utilizable with a wide variety of chest evacuation apparatus, including 1-bottle, 2-bottle, and 3-bottle assemblies. However, the accompanying drawings illustrate a preferred embodiment in which the inventive combination is utilized in a 3-bottle apparatus, including a liquid collection chamber and a water-manometer vacuum regulator chamber in addition to the water-seal chamber.

In accordance with the present invention, the water-seal chamber has one end portion communicating with a first column for receiving air from the chest cavity being evacuated, and another end portion communicating with a second column which is connectable to a regulated vacuum source. Within the water-seal chamber there is provided a fluid passage between its end portions. The passage is inclined upwardly toward the vacuum receiving end and away from the end receiving air from the chest cavity. This inclination of the passage promotes the flow of bubbles of evacuated air, the bubbles at low flow rates passing mainly along the upper portion of the passage. At least one, and preferably a plurality of air trap tubes are provided. These tubes have closed upper ends with lower ends communicating with the top portion of the inclined fluid passage. The trap tubes are inclined upwardly in the opposite direction from that of the fluid passage, that is, toward the inlet end for the air bubbles. The air trapped in the tubes is removable by tilting the water-seal chamber to elevate the lower ends of the trap tubes to release air therefrom. The trap tubes may be sized for calibration so that the volume of collected air can be visually determined, and appropriate indicia can be provided for visual reading of the volume.

The fluid passage may have an inclination of a small acute angle with respect to the horizontal, such as an inclination of from 2° to 15°. The inclination of the trap tubes is preferably somewhat greater, such as at an acute angle with respect to the horizontal of from 10° to 30°. It should be understood, however, that these angles are not critical, and are subject to variation depending on the specific design employed.

Turning now to a discussion of the drawings, FIG. 1 shows a perspective view of a 3-bottle type chest evacuation apparatus incorporating the improvement of the present invention. The evacuation apparatus A is removably mounted on a base B, and includes a liquid collection chamber L, a water-seal chamber S, and a pressure regulator chamber P. The apparatus A is assembled from two complementary transparent plastic sheets 10a and 10b. The passages and cavities in these sheets may be formed by molding or may be milled out. In the illustrations given, the passages and cavities are formed in plate 10a only. Plate 10b is a plain cover plate. The sheets 10a and 10b may be assembled by use of a suitable adhesive, which is applied to form a liquid and air-tight seals around the chambers L, S, and P. Connections are provided to these passages through openings in the top which receive tubular connectors. In the embodiment shown, tube 11 connects to a passage communicating with a liquid chamber L, tube 12 communicates with a passage connecting to the vacuum end of the water-seal chamber S. Tube 13 provides a connection to the atmosphere on one side of the pressure regulator chamber P. Extending from the nipples 11, 12, and 13, are respectively conduits 14, 15, and 16. As indicated in FIG. 2, conduit 14 receives the air and liquid from the chest catheter, conduit 15 is connected to a regulated vacuum source. Conduit 16 terminates in an opening to the atmosphere at 17.

The internal construction of the chambers and passageways within the apparatus are shown more clearly in FIG. 2. Chamber L comprises a column in vertical alignment with the discharge from tube 14. Evacuated liquid therefore falls to the bottom of the tubular chamber L and will collect therein, such as to the liquid level 19 as indicated. An outlet port 20 is provided at the lower end of chamber L, which may be selectively opened to remove the collected liquid. Liquid volume indicia may be provided (not shown) along the sides of chamber L so that the liquid volume may be observed.

Diverging from the enlarged top 20 of the liquid collection chamber L is a latterly-extending passage 21 which communicates with a vertically-extending column 22. The vacuum connection 12 communicates with a vertically-extending column 23. As will subsequently be described in detail, column 22 communicates with the air inlet end of the water-seal chamber S, and column 23 communicates with the outlet or suction end of the water-seal chamber.

The pressure regulator chamber P which functions as a manometer has an enlarged cross-section to minimize fluctuations of the water contained therein. A representative water level is indicated at 24. The space above the water manometer communicates through passage 25 with vacuum column 23. The lower end of pressure regulator chamber P communicates through a downward extending passage 25 and an angularly-extending passage 26 with a column 27 that connects to atmosphere tube 13. With this arrangement, a pressure differential will be maintained across the pressure regulator chamber, for example, 15 to 25 centimeters of water, a typical setting being 20 cm water. In the illustration given, this will represent the difference in height between the liquid level 28 and the atmosphere connection column 27 on the one side, and the liquid level 24 in the pressure regulator chamber P. Whenever a greater vacuum is applied from the vacuum source through conduit 15 which exceeds the manometer's water level (e.g., 20 cm $H_2O$ vacuum), atmospheric air will be sucked through from column 27, bubbling upwardly in chamber P and thereby providing a compensating pressure increase in column 23; thus disallowing the vacuum in column 23 to exceed that of the manometer's water level. To minimize fluctuation of the liquid P, a small auxiliary air passage 29, or a series of such passages, may be provided. Most of the compensating air flow can therefore pass through passage means 29 forming fine bubbles which will rise within the manomer chamber, avoiding large bursts of air and providing a more stable vacuum.

Description of Air Volume Meter

As shown in FIG. 2, the water-seal chamber S includes fluid passage 30 which communicates at one end with the lower end of column 22, and at its other end with the lower end of column 23. Column 23 is enlarged at its lower end to provide a liquid chamber 23a. Normally a liquid level, such as indicated at 31, is maintained with chamber 23a. The passage 30 is also maintained full of water, and the water-level extends upwardly into the lower portion of column 22, such as to the level 32. The difference between the levels 31 and 32 represents the relative amount of suction or pressure being applied to the lung cavity beyond that provided by the vacuum source. For example, this difference is typically in the range from 2 to 4 cm $H_2O$ less than the applied vacuum from column 23 when a bubble is about to cross the water seal.

Passage 30 is inclined upwardly at a small acute angle with respect to the horizontal. This inclination is in an upward direction from the lower end of column 22, the inclination being sufficient to promote a slow flow of air bubbles through passage 30. The top portion of passage 30 communicates with at least one, and preferably a plurality, of air trap tubes. In the illustration given, three such tubes are shown, respectively designated by the numbers 33, 34, and 35.

As will be noted, the trap tubes are arranged in generally parallel alignment and are disposed at an acute angle with respect to the horizontal. More specifically, trap tubes 33, 34, and 35 are inclined upwardly away from the suction end of passage 30 where it connects to column 23, and toward the air inlet end of passage 30 where it connects to column 32. These tubes provide air collection chambers which may be calibrated so that the volume of collected air can be visually determined. For example, as shown, they may have the same cross-sections but different lengths. Increasingly larger air collection chambers are thereby provided from tube 33 to tube 34 to tube 35. The upper ends of these tubes are closed and their lower ends 33a, 34a, and 35a communicate with the top portion of passage 30 so that air bubbles passing along the upper portion of passage 30 enter the collection chambers formed by the tubes 33, 34, and 35.

Passage 30 need only be inclined at a small acute angle with respect to the horizontal, for example, from 2° to 15°. In the illustration given, the passage inclination is approximately 5°. Preferably the air trap tubes are inclined at a somewhat larger acute angle with respect to the horizontal, but still at a relatively small acute angle, such as less than 45°. Typically, air trap tubes may be inclined at an angle of from 10° to 30°. As shown in the drawing, the air trap tubes are inclined at an angle with respect to the horizontal of about 20°.

The operation of the air meter is illustrated particularly in FIG. 4. Air being drawn downwardly through column 22 enters the water in the water-seal chamber S, forming small bubbles as indicated at 36. The bubbles move into inclined passage 30, tending to flow along the upper portion of the passage, as indicated. At the beginning of the air collection, all of the trap tubes 33, 34, and 35 are filled with water as indicated in FIG. 2. Air bubbles first enter the lower end 33a of tube 33. When that tube becomes filled with air, the bubbles then flow past the entrance to tube 33 and enter the mouth 34a of tube 34. As shown in FIG. 4, the air collection has proceeded to the point where both tubes 33 and 34 are essentially filled with air. At that time, the bubbles then move on upwardly in passage 30, entering mouth 35a and begin to collect in the upper end of tube 35, as indicated.

The volume of collected air can be visually determined by calibrating the tubes 33, 34, and 35, and providing numerical indicia associated with the tubes. For example, as shown in FIG. 4, tubes can be calibrated for a volume of from 0 to 12 milliliters (ml). As shown, tube 33 when filled will contain approximately 2 ml air, tube 34 approximately 4 ml air, and tube 36 approximately 6 ml air, making a total volume of at least 12 ml. For example, with the air having been collected as illustrated in FIG. 4, it can be visually determined that 7 ml air have been collected, representing the amount removed from the lungs between the start of the collection and the reading time. As previously indicated, observation of the collection of such small volumes of air is particularly useful in the management of pleural catheters.

Figure 5:
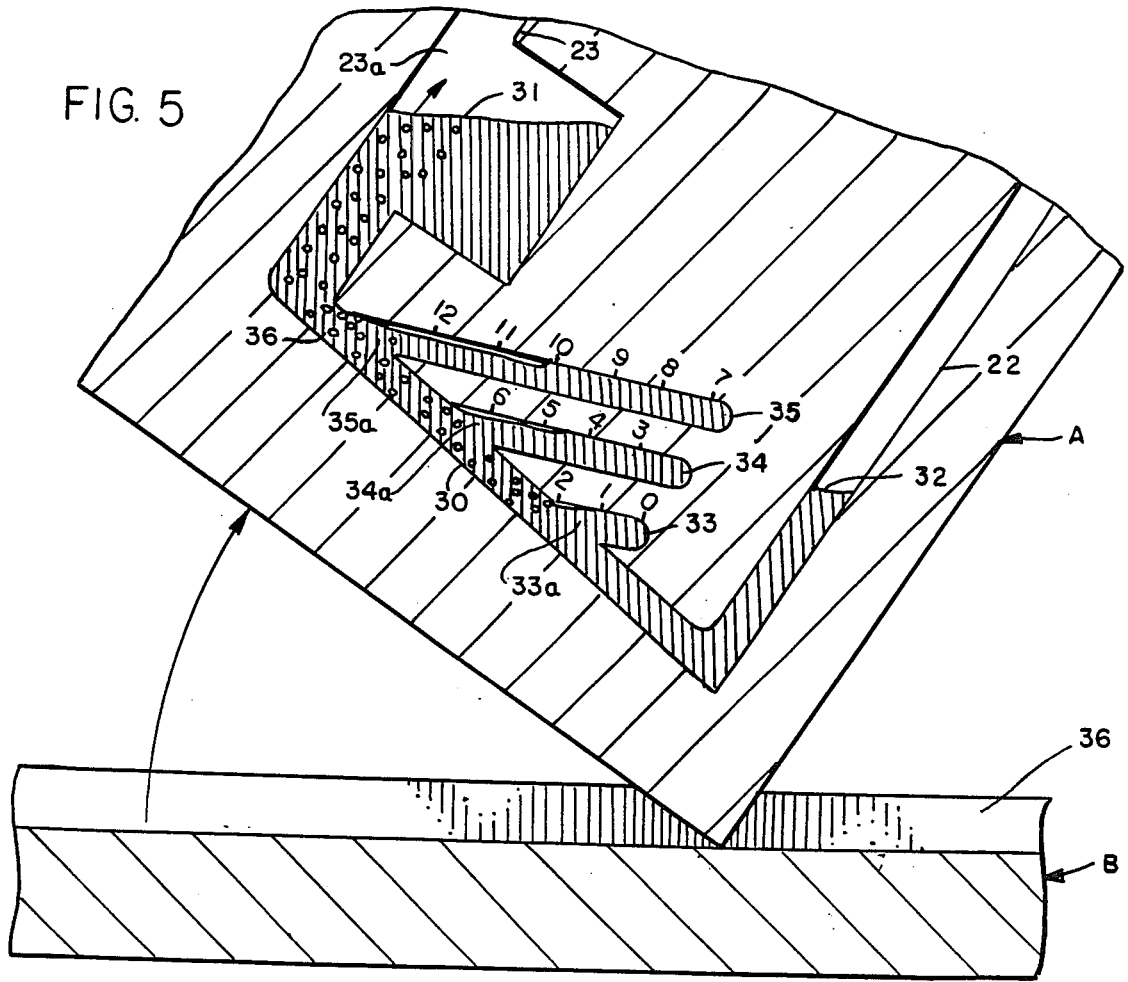
FIG. 5 is a sectional view similar to FIG. 4 showing the water-collection chamber tilted for removal of air from the air traps for resetting of the meter.

FIG. 5 illustrates the method of resetting the air meter. As shown, the assembly A is supportably received in a groove 36 from which it can be lifted and tilted as illustrated in FIG. 5. By elevating the lower ends of the trap tubes, the air collected therein can be released. The trapped air flows out along the upper walls of the tube traps as they are brought to a horizontal alignment or to a slightly upward inclination. Reformed bubbles 36 then pass upwardly into the tube section 23a. This can be accomplished while maintaining the water seal. After the air has been released and the trap tubes have been refilled with water, the apparatus A is reseated on the base B. It should be understood that the use of a support base is not required and that other means can be provided for supporting the apparatus A which permit it to be tilted for resetting the air volume meter.

The cross-sectional configuration of the passage 30 and trap tubes 33, 34, and 35 can be varied. In the illustration given, as shown in FIG. 3, both passage 30 and trap tube 35 have rectangular cross-sections. In this embodiment, the cross-sections of trap tubes 33 and 34 have similar shapes. However, other cross-sectional shapes can be employed, such as square, circular, etc. It is desirable to have a cross-sectional shape which can be easily correlated with volumetric measurement.

I claim:

1. A chest cavity evacuation apparatus including a water-seal chamber having one end portion communicating with a first column for receiving air from the chest cavity being evacuated and another end portion communicating with a second column which is connectable to a vacuum source, wherein the improvement comprises providing in said water-seal chamber a fluid passage extending between said end portions, said fluid passage being inclined upwardly toward said other end to promote the flow of bubbles of evacuated air therethrough, at least one air trap tube having a closed upper end and a lower end communicating with the top portion of said passage, said trap tube being inclined upwardly toward said one end, the air trapped in said tube being removable by tilting said water-seal chamber to elevate the lower end of the trap tube to release the air therefrom.

2. The apparatus of claim 1 in which said trap tube is sized for calibration so that the volume of collected air can be visually determined.

3. The apparatus of claim 1 in which said trap tube is inclined at an acute angle with respect to the horizontal of from 10° to 30°.

4. The apparatus of claim 1 or claim 3 in which said fluid passage is inclined at an angle with respect to the horizontal of from 2° to 15°.

5. A chest cavity evacuation apparatus including a horizontally-extending water-seal chamber having one end portion communicating with a first vertically-extending column for receiving air from the chest cavity being evacuated and another end portion communicating with a second vertically-extending column which is connectable to a vacuum source, wherein the improvement comprises providing in said water-seal chamber a fluid passage extending between said end portions, said fluid passage being inclined upwardly toward said other end to promote the flow of bubbles of evacuated air there through, a plurality of air trap tubes having closed upper ends and being disposed in sequence along said fluid passage with their lower ends communicating at sequential points with the top portion of said passage, said trap tubes being generally arranged in parallel alignment and being inclined upwardly toward said one end, the air trapped in said tubes being removable by tilting said water-seal chamber to elevate the lower ends of the trap tubes to release air therefrom.

6. The apparatus of claim 5 in which said trap tubes are sized for calibration so that the volume of air collected can be visually determined.

7. The apparatus of claim 5 in which said trap tubes are inclined at an acute angle with respect to the horizontal of from 10° to 30°.

8. The apparatus of claim 5 or claim 7 in which said fluid passage is inclined at an angle with respect to the horizontal of from 2° to 15°.

* * * * *